United States Patent [19]

Kinast et al.

[11] 4,246,345

[45] Jan. 20, 1981

[54] PROCESS FOR THE PRODUCTION OF 6-AMINO-6-DEOXY-L-SORBOSE

[75] Inventors: Günther Kinast; Michael Schedel, both of Wuppertal, Fed. Rep. of Germany

[73] Assignee: Bayer Aktiengesellschaft, Leverkusen, Fed. Rep. of Germany

[21] Appl. No.: 56,741

[22] Filed: Jul. 11, 1979

[30] Foreign Application Priority Data

Aug. 3, 1978 [DE] Fed. Rep. of Germany ....... 2834122

[51] Int. Cl.$^3$ ............................................. C12P 19/26
[52] U.S. Cl. ....................................... 435/84; 435/822; 435/812
[58] Field of Search ................................. 435/84, 122

[56] References Cited

U.S. PATENT DOCUMENTS

| | | | |
|---|---|---|---|
| 3,634,197 | 1/1972 | Umezawa | 435/84 |
| 3,998,698 | 12/1976 | Argoudelis et al. | 435/84 |

*Primary Examiner*—Alvin E. Tanenholtz
*Attorney, Agent, or Firm*—Sprung, Felfe, Horn, Lynch & Kramer

[57] ABSTRACT

The invention relates to a process for the production of 6-amino-6-deoxy-L-sorbose which comprises culturing an aerobic micro-organism capable of oxidizing 1-amino-1-deoxy-D-glucitol or an enzymatic extract obtained from said aerobic micro-organism under aerobic conditions and at a suitable temperature in an aqueous nutrient medium containing 1-amino-1-deoxy-D-glucitol or a salt thereof and also containing assimilable sources of carbon, nitrogen and essential trace element to impart said 6-amino-6-deoxy-L-sorbose to said aqueous nutrient medium.

7 Claims, No Drawings

PROCESS FOR THE PRODUCTION OF 6-AMINO-6-DEOXY-L-SORBOSE

The present invention relates to a new microbiological process for the production of 6-amino-6-dexoy-L-sorbose from 1-amino-1-deoxy-D-glucitol.

6-Amino-6-deoxy-L-sorbose of the formula

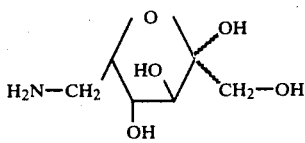
(I)

has hitherto been prepared from sorbose in an 8-stage synthesis by a purely chemical route (H. Paulsen, I. Sangster and H. Heins, Chem. Ber. 100, 802 to 815 (1967)).

6-Amino-6-deoxy-L-sorbose is in the furanose form (Ia) in an acid medium, and in an alkaline medium is in the piperidinose form (Ib), which is in equilibrium with the compound (Ic).

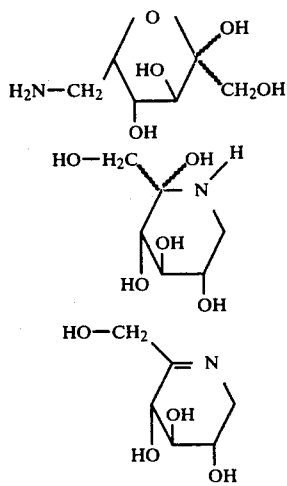

Ia

Ib

Ic

The compounds (Ia), (Ib) and (Ic) are highly unstable and in aqueous solution, especially in the acid pH range, undergo irreversible rearrangement, by the elimination of water, to the pyridine derivative of the following formula:

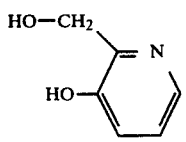
(II)

It is also known (J. K. N. Jones, M. B. Perry and J. C. Turner, Can. J. Chem. 39, 2400–2410 (1961) that 6-deoxy-6-N-methylacetamido-L-sorbose can be prepared in 36% yield from 1-deoxy-1-N-methylacetamide-D-glucitol by a 19-day microbiological oxidation with Acetobacter suboxidans. This disadvantage of this reaction is, on the one hand, the long reaction time and on the other hand the fact that the amino group must be protected by acetylation. Because of the chemical instability of (I), it is to be expected that it will not be possible to convert 6-deoxy-6-N-methylacetamido-L-sorbose to the unprotected 6-deoxy-6-methylamino-L-sorbose. Thus, 6-amino-6-deoxy-L-sorbose (I) cannot be prepared by this process.

According to the present invention we provide a process in which 6-amino-6-deoxy-L-sorbose is obtained when 1-amino-1-deoxy-D-glucitol or a salt thereof is oxidised with either an aerobic micro-organism or with an extract obtained from an aerobic microorganism, which is capable of catalysing the oxidation, in suitable media and under suitable conditions. The reaction is as follows:

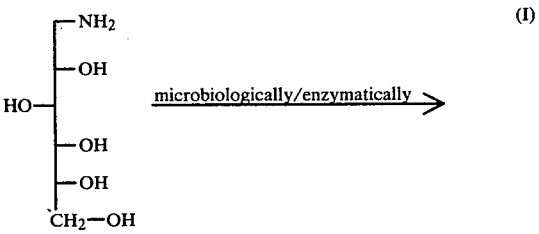
(I)

Under favourable conditions, the microbiological/enzymatic oxidation of 1-amino-1-deoxy-D-glucitol to 6-amino-6-deoxy-L-sorbose is complete after a few hours. With this short reaction period, decomposition of 6-amino-6-deoxy-L-sorbose is so slight that it can be disregarded.

The desired product can be isolated as such or can be further reacted, for example to 1-deoxy-nojirimicin (III) by catalytic hydrogenation

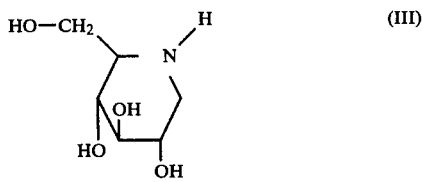
(III)

It is to be regarded as extremely surprising that 6-amino-6-deoxy-L-sorbose is obtained in a simple manner, in a short time and in high yield by the microbiological/enzymatic process according to the invention. In view of the state of the art it was to be expected that it would be possible to oxidise only 1-amino-1-deoxy-D-glucitols in which the nitrogen is protected, for example by acetyl, with micro-organisms to give the corresponding amino-L-sorboses in which the nitrogen is protected and subsequently to isolate the said products (J. K. N. Jones, M. B. Perry and J. C. Turner, Can. J. Chem. 39, 2400–2410 (1961)), because during the fermentation period of several days, which has been described, 6-amino-6-deoxy-L-sorbose, in an aqueous medium in the pH range employed, reacts further to give the undesired pyridine derivative (II).

The starting material employed in the process according to the invention, that is to say 1-amino-1-deoxy-D-glucitol, is known; it can be prepared, for example, from D-glucose by reductive amination with ammonia, hydrogen and nickel as the catalyst. The starting material can be employed as such or in the form of a salt thereof, for example in the form of the chloride, sulphate, nitrate, acetate, oxalate or dihydrogen phosphate.

Micro-organisms which are suitable for carrying out the process according to the invention, or from which active extracts for carrying out the process according to the invention can be obtained, can be Procaryotes, that is to say bacteria, or Eucaryotes, for example fungi, and in each case can belong to very diverse taxonomic groups. Those skilled in the field of microbiology can easily find suitable micro-organisms by cultivating a relatively large number of aerobic or facultatively aerobic micro-organisms, such as are available, for example, from public collections, in a corresponding nutrient medium which contains 1-amino-1-deoxy-D-glucitol and testing their ability to catalyse the oxidation reaction according to the invention and to accumulate 6-amino-6-deoxy-L-sorbose.

Following this procedure, it has been found that, for example, bacteria of the order Pseudomonadales, and within this order in particular representatives of the family Pseudomonadaceae and amongst these in particular bacteria of the genus Gluconobacter, are suitable micro-organisms for the process according to the invention. Furthermore, bacteria from the group of the coryneform bacteria, especially those of the genus Corynebacterium, have also proved suitable. It has been found to be possible to carry out the process according to the invention with fungi, for example, with yeasts of the order Endomycetales, especially with those of the family Spermophthoraceae and amongst these in the main with representatives of the genus Metschnikowia.

Particularly preferred examples which may be mentioned are: Gluconobacter oxidans ssp. suboxydans (DSM 50 049), Glucobacter oxidans ssp. suboxydans (DSM 2003), Corynebacterium betae (DSM 20141) and Metschnikowia pulcherrima (ATCC 20 515). Such micro-organisms may be used in the form of a growing culture, a concentrated cell suspension, a non-fractionated crude extract or a purified extract fraction.

The DSM numers give the numbers under which the said micro-organisms are filed in the Deutsche Sammlung von Mikroorganismen (German Collection of Micro-organisms), Göttingen. Metschnikowia pulcherrima is filed in the American Type Culture Collection, Rockville, Maryland USA.

If the process according to the invention is carried out with intact micro-organisms in a growing culture, solid, semi-solid or liquid nutrient media can be used. Aqueous-liquid nutrient media are preferably used.

The culture can be carried out in all nutrient media which it is known to use for cultivation of micro-organisms of the above-mentioned groups and which contain the 1-amino-1-deoxy-D-glucitol which is to be oxidised by the process according to the invention. The nutrient medium must contain sources of assimilable carbon and nitrogen, as well as mineral salts. Suitable sources of assimilable carbon and nitrogen are, in particular, complex mixtures, such as those constituted, in particular by biological products of diverse origin, for example soy bean flour, cotton seed flour, lentil flour, pea flour, soluble and insoluble vegetable proteins, corn steep liquor, yeast extract, peptones and meat extracts. Additional sources of nitrogen are ammonium salts and nitrates, for example ammonium chloride, ammonium sulphate, sodium nitrate and potassium nitrate. The mineral salts, which should be contained in the nutrient medium, provide, for example, the following ions: $Mg^{++}$, $Na^+$, $K^+$, $Ca^{++}$, $NH_4^+$, $Cl^-$, $SO_4^{--}$, $PO_4^{---}$ and $NO_3^-$ and also ions of the customary trace elements such as Cu, Fe, Mn, Mo, Zn, Co and Ni.

If these salts and trace elements are not present in sufficient amounts in the said complex constituents of the nutrient medium or in the water used it is appropriate to supplement the nutrient medium accordingly.

The 1-amino-1-deoxy-D-glucitol to be oxidised in the process according to the invention can be added to the base nutrient medium either on its own or as a mixture with one or more oxidisable compounds. Additional oxidisable compounds which can be used are primary alcohols (e g. $C_1$-$C_5$-alkanols, alkanediols and alkanetriols), for example ethanol, secondary alcohols, for example isopropanol, polyols, for example sorbitol or glycerol; aldehydes, for example glycolaldehyde, aldoses, for example glucose or gluconic acids.

If one or more of the said compounds are added to the nutrient solution, the 1-amino-1-deoxy-D-glucitol to be oxidised can be added either prior to inoculation or at any desired later point in time between the early log phase and the late stationary growth phase. In such a case the particular organism is pre-cultured on the particular oxidisable compounds added.

A pH range of between 2 and 10 is suitable for the process according to the invention. It is advantageous to buffer the culture in this range, for example with phosphate buffer or acetate buffer.

As is customary in fermentation technology, the pH can also be regulated automatically, sterile organic or inorganic acid, for example sulphuric acid, or sterile alkali, for example sodium hydroxide solution, being added to the culture solution at intervals.

As is generally the case for microbiological processes, foreign infection of the culture media should be avoided. For this purpose, the customary precautions are taken, such as sterilisation of the nutrient media, of the culture vessels and of the air required for aeration. It is possible to use, for example, steam sterilisation or dry sterilisation for sterilisation of the culture vessels; air and the culture media can likewise be sterilised by steam or also by filtration.

The inoculation of the nutrient media is effected by generally customary methods, for example by means of slanted tube cultures or flask cultures.

The culture is effected under aerobic conditions and can be carried out in accordance with the generally customary methods, for example using shaking cultures, for example in shaking flasks, air-agitated cultures or submersion cultures. Preferably, the culture is carried out by the aerobic submersion procedure in aerated fermenters, for example in conventional submersion fermentation tanks. It is possible to carry out the culture continuously or discontinuously. Preferably, the discontinuous procedure is employed.

It is appropriate to ensure that the micro-organisms are adequately brought into contact with oxygen and the nutrients. This can be effected by the generally customary method, such as shaking and stirring.

If foam forms in an undesired amount during the cultivation the customary chemical foam control agents, for example liquid fats and oils, oil-in-water emulsions, paraffins, higher alcohols, such as octadecanol, silicone oils, polyoxyethylene compounds and polyoxypropylene compounds, can be added. Foam can also be suppressed or eliminated with the aid of the customary mechanical devices.

The culture temperature can be between about 20° and about 45° C. The culture period can be varied greatly and, for example, the composition of the nutrient medium and the culture temperature play a role.

The conditions which are optimum in a particular case can be determined easily by any specialist in the field of microbiology.

It has been found that the amount of 6-amino-6-deoxy-L-sorbose which accumulates in the culture broth generally reaches its maximum between 5 hours and 5 days after adding 1-amino-1-deoxy-D-glucitol.

It is also possible to carry out the oxidation reaction according to the invention with concentrated cell suspensions of suitable micro-organisms. Concentrated cell suspensions are prepared as follows: The micro-organisms which can be used are cultured in a suitable nutrient solution, then harvested, for example by centrifuging, and suspended in a smaller volume of the same nutrient solution or in salt or buffer solutions, for example physiological sodium chloride solution or aqueous solutions of $KH_2PO_4$, Na acetate or maleate or simply in tap water or distilled water. 1-Amino-1-deoxy-D-glucitol is then added to a cell suspension of this type and the oxidation reaction according to the invention is carried out under the conditions described above for growing cultures.

The advantage of this process is the shortening of the reaction time of the process according to the invention to a few hours, which is made possible by the higher concentration of micro-organisms.

It is also possible to carry out the process according to the invention not only with growing cultures of micro-organisms or with concentrated cell suspensions obtained therefrom but also with extracts or extract fractions prepared from these bacteria. The extracts can be crude extracts, such as are obtained by conventional digestion of micro-organism cells. Methods to break up cells which can be used are: ultrasonic treatment, passage through a French pressure cell, grinding with quartz sand, incubation with enzymes to induce lysis, autolysis or repeated freezing and thawing.

If non-fractionated crude extracts are used for the oxidation of 1-amino-1-deoxy-D-glucitol to 6-amino-6-deoxy-L-sorbose, the reaction conditions which have proved advantageous are, in principle, the same as those which have been described for carrying out the process according to the invention with growing or testing micro-organism cells.

If the process according to the invention is to be carried out with partially purified extract preparations (enzymes), the generally customary methods of protein chemistry, such as ultracentrifuging, precipitation reactions, ion exchange chromatography or adsorption chromatography, gel filtration or electrophoretic methods, can be employed to obtain such preparations. In order to clarify the question as to which of several fractions obtained by one of the said methods is suitable for catalysis of the oxidation reaction according to the invention, an aliquot of this fraction is mixed with 1-amino-1-deoxy-D-glucitol at a temperature between 20° and 45° C. and a pH of between 2 and 10 and the mixture is tested to determine the formation of 6-amino-6-deoxy-L-sorbose with the aid of the increase in the saccharase inhibitory activity (see below). In order to carry out the reaction according to the invention with fractionated cell extracts, it can be necessary to add to the assay system additional reactants such as, for example, physiological or synthetic electron acceptors, say $NAD^+$, $NADP^+$, methylene blue, dichlorophenol-indophenol, tetrazolium salts and the like. If such additional reactants have to be added, these can be employed either in substrate amounts, that is to say in concentrations which correspond to that of the 1-amino-1-deoxy-D-glucitol employed, or in catalytic amounts, that is to say in concentrations which are markedly below the chosen concentration of 1-amino-1-deoxy-D-glucitol.

If, in the second case, it is to be ensured that the process according to the invention is carried out approximately quantitatively, a system which continuously regenerates the reactant which is present only in a catalytic amount must also be added to the reaction mixture. This system can be, for example, an enzyme which ensures the reoxidation, in the presence of oxygen or other oxidising agents, of an electron acceptor which is reduced in the course of the reaction according to the invention.

In other respects, the same conditions as those which have been indicated above for the oxidation of 1-amino-1-deoxy-D-glucitol to 6-amino-6-deoxy-L-sorbose in growing micro-organism cultures or concentrated cell suspensions have also proved advantageous for carrying out the process according to the invention with fractionated cell extracts. In particular the temperature range is from 20° to 45° C. and the pH range from 2 to 10 in this case also. However, the amount of 6-amino-6-deoxy-L-sorbose formed reaches its maximum in a shorter time. Depending on the concentration of the extract, an incubation time of between 2 hours and 3 days suffices.

The time-dependent formation of 6-amino-6-deoxy-L-sorbose in the culture medium can be followed either by thin layer chromatography or with the aid of the increase in the inhibitory activity in the saccharase inhibition test, preferably by the second method.

The saccharase inhibition test in vitro enables the enzyme-inhibitory activity of a substance to be determined by comparison of the activity of the solubilised intestinal disaccharidase complex in the presence and in the absence (so-called 100% value) of the inhibitor. A virtually glucose-free sucrose (glucose<100 ppm) is used as the substrate which determines the specificity of the inhibitor test. The determination of the enzyme activity is based on the determination, by spectrophotometry, of liberated glucose by means of glucose dehydrogenase and nicotinamide/adenine dinucleotide as the cofactor.

The intestinal disaccharidase complex is obtained from the small intestine mucosa of pigs by tryptic digestion, precipitation from 66% strength ethanol at −20° C., taking up the precipitate in 100 mM phosphate buffer (pH 7.0) and finally carrying out dialysis against the same buffer.

100 μl of a dilute solution of the intestinal disaccharidase complex in 0.1 M maleate buffer (pH 6.25) are added to 10 μl of a sample solution, which is made up so that the extinction of the test mixture is at least 10% but not more than 25% below that of the 100% value, and the mixture is pre-incubated for 10 minutes at 37° C. The activity of the dilute solution of the disaccharidase complex must be adjusted to 0.1 SU/ml.

One saccharase unit (SU) is defined as that enzyme activity which splits one μmol of sucrose per minute at 37° C. and thus results in the release of 1 μmol of glucose, which is determined in the test, and 1 μmol of fructose, which is not determined in the test.

The saccharolytic reaction is then started by adding 100 μl of a 0.4 M solution of sucrose in 0.1 M maleate buffer (pH 6.25) and, after an incubation period of 20 minutes at 37° C., is stopped by adding 1 ml of glucose dehydrogenase reagent (lyophilised glucose dehydrogenase/mutarotase mixture and 331.7 mg of β-nicotinamide-adenine dinucleotide (free acid), dissolved in 250 ml of 0.5 M tris buffer of pH 7.6). In order to detect the glucose, the mixture is incubated for 30 minutes at 37° C. and is then analysed by photometry at 340 nm against a reagent blank (with enzyme but without sucrose).

In order to enable the content of the oxidation product according to the invention, that is to say 6-amino-6-deoxy-L-sorbose, in the supernatant liquor of the culture to be determined from the inhibition found in the saccharase inhibition test, increasing amounts of pure 6-amino-6-deoxy-L-sorbose were employed in the saccharase inhibition text, under otherwise identical conditions, and the inhibition found was plotted in percent against the concentration of 6-amino-6-deoxy-L-sorbose in the test. A hyperbolic inhibitory curve was obtained. The inhibitor concentration which resulted in a 50% inhibition of the saccharase from the small intestine mucosa of pigs was determined from this standard curve as 1.2 μg of 6-amino-6-deoxy-L-sorbose/ml of test batch. The standard curve was used as the basis for the determination of the content of 6-amino-6-deoxy-L-sorbose in the supernatant liquor of the culture.

The 6-amino-6-deoxy-L-sorbose obtained according to the invention is isolated from the culture solution as follows: The cell mass is filtered off or centrifuged off and the supernatant liquor is passed through a column containing acid ion exchanger and rinsed with water. Elution is then carried out with 0.3 N hydrochloric acid and the eluate is concentrated. After adding ethanol, the hydrochloride of 6-amino-6-deoxy-L-sorbose crystallises out. The compound obtained according to the invention has physical data which are the same as those quoted in the literature:

melting point: 127° to 129° C. (with decomposition).

If it is intended to carry out further processing of the compound to be prepared according to the invention to 1-deoxy-nojirimicin, isolation can be dispensed with. For this purpose, the clear solution, after removal of the cell mass, is hydrogenated with a catalyst, such as Pd-on-charcoal, Raney nickel or PtO2, and with hydrogen under a pressure of 1 to 80 bars. After removing the catalyst, 1-deoxy-nojirimicin is isolated by chromatography on an acid ion exchanger. The 1-deoxy-nojirimicin thus obtained agrees with authentic samples in respect of all the physical characteristics.

1-Deoxynojirimycin is identical with 2-Hydroxymethyl-3,4,5-trihydroxypiperidine and is useful as an antidiabetic agent and as an inhibitor of increased lipid biosynthesis U.S. Pat. No. 4,065,562).

In both working up procedures, unconverted 1-amino-1-deoxy-D-glucitol or its salts are recovered by the chromatography on an ion exchanger and can be re-used as starting material for the process according to the invention.

EXAMPLE 1

Oxidation of 1-amino-1-deoxy-D-glucitol by Glucobacter oxidans ssp. suboxidans in a growing culture Glucobacter oxidans ssp. suboxidans is pre-cultured in a liquid nutrient solution which contains, per liter, 20 g of yeast extract, 200 g of sorbitol and 10 g of KH2PO4 dissolved in demineralised water. The pH value of the nutrient solution for the pre-culture is adjusted to 5.0 and 100 ml amounts of the solution are introduced into 1 l conical flasks and sterilised by heating in an autoclave at 121° C. for 15 minutes. The oxidation of 1-amino-1-deoxy-D-glucitol is carried out in a nutrient solution which contains, per liter, 20 g of yeast extract, 200 g of sorbitol, 10 g of KH2PO4 and 10 g of 1-amino-1-deoxy-D-glucitol (oxalate salt) dissolved in demineralised water. The pH value is adjusted to pH 5.0 with dilute hydrochloric acid. 100 ml amounts of the nutrient solution are introduced into 1 l conical flasks are sterilised by heating at 121° C. in an autoclave for 15 minutes. After cooling, each flask is inoculated with 2 ml of the preculture and the flasks are then incubated at 28° C. on a shaking machine at 280 revolutions per minute. The formation of 6-amino-6deoxy-L-sorbose is followed by examining a correspondingly dilute sample of the supernatant liquor of the culture in the saccharase inhibition test. The fermentation is discontinued at the time the concentration of 6-amino-6-deoxy-L-sorbose reached its maximum (3.8 g/l after 1 day, which corresponds to 38% conversion). The culture broths from 10 batches carried out in parallel are combined, so that a volume of 1 l was available for working up.

The cells are separated off by centrifuging, the filtrate is allowed to run through a column (40 cm long, 2 cm in diameter) filled with strongly acid ion exchanger Lewatit TSW 40, the column is rinsed with water and the product is eluted with 0.3 normal hydrochloric acid. The eluate is concentrated to a syrup of low viscosity and ethanol was added until the mixture became turbid. The hydrochloride of 6-amino-6-deoxy-L-sorbose crystallises in an ice bath.

Melting point: 127° to 129° C. (with decomposition); Hans Paulsen, Ian Sangster and Kurt Heyns, Chem. Ber. 100, 802–815 (1967):

Melting point: 127° to 129' C. (with decomposition).

EXAMPLE 2

Oxidation of 1-amino-1-deoxy-D-glucitol by Gluconobacter oxidans ssp. suboxydans in a growing culture in a fermenter Gluconobacter oxydans ssp. suboxydans is precultured on slanted tubes. The nutrient medium contains, per 1 l, 10 g of yeast extract, 100 g of sorbitol and 2 g of KH2PO4, dissolved in tap water. Using a tube with a good growth, a liquid culture of 250 ml of the same medium but without agar in a 1 l conical flask is inoculated and incubated overnight at 28° C. on a circular shaking machine at 280 rpm. A 10 l fermenter, which is charged with a liquid medium which contains, per 1 l 10 g of yeast extract, 100 g of sorbitol, 2 g of KH2PO4 and 10 g of 1-amino-1-deoxy-D-glucitol (HCl salt) is inoculated with this second pre-culture. The pH value had been adjusted to 6.2. The medium had been sterilised by heating at 125° C. for 60 minutes. 5 l of air per minute are blown through the fermenter, and the fermenter is stirred at 500 rpm. The incubation temperature is 28° C. Samples are taken under sterile conditions at various times and the content of 6-amino-6-deoxy-L-sorbose is determined with the aid of the saccharase inhibition activity. After 1½ days, 2.6 g/l of 6-amino-6-deoxy-L-sorbose are present; this corresponds to a conversion of 26%. The cells are centrifuged off from the culture broth and the clear supernatant liquor is worked up as indicated in Example 1.

EXAMPLE 3

Oxidation of 1-amino-1-deoxy-D-glucitol by Corynebacterium betae in a growing culture.

Corynebacterium betae is pre-cultured on slanted tubes which contain the following nutrient media: 10 g/l of tryptically digested casein peptone, 6 g/l of yeast extract, 5 g/l of sorbitol, 5 g/l of NaCl and 20 g/l of agar in demineralized water. Using a slanted tube with a good growth, 250 ml of liquid nutrient solution (in a 1 l conical flask), which contains, per 1 l 10 g of tryptically digested casein peptone, 5 g of yeast extract, 5 g of sorbitol, 5 g of NaCl and 2 g of 1-amino-1-deoxy-D-glucitol (oxalate salt), are inoculated. The constituents of the nutrient medium are dissolved in demineralised water and sterilised by heating in an autoclave at 121° C. for 20 minutes. The culture is incubated at 37° C. on a rotary shaker at 200 rpm. The content of 6-amino-6-deoxy-L-sorbose in the culture broth is followed by measuring the saccharase inhibitory activity. After 1½ days 0.15 g/l was present; this corresponds to a conversion of 7.5%. The fermentation is discontinued at this time, the cells are separated off by centrifugation and the clear supernatant liquor of the culture is worked up as indicated in Example 1.

EXAMPLE 4

Oxidation of 1-amino-1-deoxy-D-glucitol by Metschnikowia pulcherrima in a growing culture Metschnikowia pulcherrima is pre-cultured in slanted tubes on a medium which contains, per 1 l 3 g of yeast extract, 6 g of peptone, 10 g of glucose, 8 g of NaCl and 20 g of agar is demineralised water. Using a slanted tube with a good growth, 250 ml of liquid medium (in a 1 l conical flask), which contains, in 1 l 3 g of yeast extract, 6 g of peptone, 10 g of sorbitol and 8 g of NaCl dissolved in demineralised water and has been sterilised by heating in an autoclave for 20 minutes at 121° C., are inoculated. The culture is incubated at 35° C. on a rotary shaker at 200 rpm. The content of 6-amino-6-deoxy-L-sorbose in the culture broth is followed with the aid of the saccharase inhibitory activity. After 2 days 0.1 g/l is present; this corresponds to a conversion of 5%. The fermentation is discontinued at this time, the cells are separated off by centrifuging and the clear supernatant liquor of the culture is worked up as indicated in Example 1.

EXAMPLE 5

Oxidation of 1-amino-1-deoxy-D-glucitol by a concentrated cell suspension of Glucobacter oxydans ssp. suboxydans Glucobacter oxydans ssp. suboxydans is cultured on a 10 l scale in a fermenter in a medium which contains, per 1 l, 100 g of sorbitol, 20 g of yeast extract and 2 g of KH₂PO₄-dissolved in tap water. 5 l of air per minute are blown through the fementer and the fermenter is stirred at 500 rpm and kept at a temperature of 30° C. After a 10 hour incubation period, the cells are centrifuged off from the culture broth and suspended in 1 l of a medium which contains 20 g of yeast extract, 2 g of KH₂PO₄ and 10 g of 1-amino-1-deoxy-D-glucitol (oxalate salt). This 10-fold concentrated cell suspension is incubated at 30° C. in a 1 l fermenter, 5 l of air per minute are blown through and the suspension is stirred at 500 rpm. After 9 hours, the cells are centrifuged off and the supernatant liquor, which at this time contains 4.1 g/l of 6-amino-6-deoxy-L-sorbose—corresponding to a 41% conversion—is worked up as indicated in Example 1.

EXAMPLE 6

Oxidation of 1-amino-1-deoxy-D-glucitol by a cell-free extract of Glucobacter oxydans ssp. suboxydans Glucobacter oxydans ssp. suboxydans is cultured, on a 10 l scale, in a fermenter in a medium which contains, per 1 l, 100 g of sorbitol, 20 g of yeast extract and 2 g of KH₂PO₄—dissolved in tap water. 5 l of air per minute are blown through the fermenter and the fermenter is stirred at 500 rpm and kept at a temperature of 30° C. After a 16 hour incubation period, the cells are centrifuged off from the culture broth, washed once by suspending in 10 mM KH₂PO₄ and again centrifuging and then suspended in 300 ml of 10 mM KH₂PO₄. The cell suspension thus obtained is broken up by passing twice through a French pressure cell under 8 bars. The cell-free extract is introduced into a 1 l conical flask, 1-amino-1-deoxy-D-glucitol (oxalate salt) is added to give a concentration of 10 g/l and the mixture is incubated at 30° C. on a rotary shaker at 280 rpm. After 7 hours it is possible to detect 3.7 g/l of 6-amino-6-deoxy-L-sorbose—corresponding to a 37% conversion—in this extract, with the aid of the saccharase inhibitory activity. The reaction is discontinued at this time and the extract is worked up as indicated in Example 1.

EXAMPLE 7

Oxidation of 1-amino-1-deoxy-D-glucitol in a defined enzyme reaction in a cell-free extract of Glucobacter oxydans ssp. suboxydans A cell-free extract of Glucobacter oxydans ssp. suboxydans is prepared as indicated in Example 6. The following are added to the extract: NADP (Na salt) to a concentration of 0.2 mM, a microsomal crude fraction from Saccharomyces cerevisiae (to a concentration of 1 mg protein/ml) as NADP-regenerating system, and 1-amino-1-deoxy-D-glucitol (oxalate salt) to a concentration of 10 g/l.

The mixture is incubated at 30° C. in a water bath and oxygen is blown through. The formation of 6-amino-6-deoxy-L-sorbose is measured with the aid of the increase in the saccharase inhibitory activity. After 7 hours, a 6-amino-6-deoxy-L-sorbose content of 3.7 g per 1 l is detectable—corresponding to a 37% conversion. The reaction is discontinued at this time and the mixture is worked up as indicated in Example 1.

What is claimed is:

1. A process for the production of 6-amino-6-deoxy-L-sorbose which comprises culturing an aerobic micro-organism capable of oxidizing 1-amino-1-deoxy-D-glucitol or an enzymatic extract obtained from said aerobic micro-organism under aerobic conditions and at a suitable temperature in an aqueous nutrient medium containing 1-amino-1-deoxy-D-glucitol or a salt thereof and also containing assimilable sources of carbon, nitrogen and essential trace elements to impart said 6-amino-6-deoxy-L-sorbose to said aqueous nutrient medium.

2. A process according to claim 1, in which the aerobic micro-organism used is of the order Pseudomonadales, is a coryneform bacteria or is a yeast of the order Endomycetales.

3. A process according to claim 1, in which the micro-organism employed is selected from *Gluconobacter oxidans* ssp. *suboxidants* (DSM 50 049), *Glucobacter oxidans* ssp. *suboxidans* (DSM 2003), *Cornynebacterium*

*betae* (DSM 20 141) and *Metschnikowia pulcherrima* (ATCC 20 515).

4. A process according to claim 3 wherein the micro-organism is used as a growing culture.

5. A process according to claim 3, in which the micro-organism is used in the form of a concentrated cell suspension.

6. A process according to claim 3, in which the micro-organism is used in the form of a non-fractionated crude extract.

7. A process according to claim 3, in which a micro-organism is used in the form of a purified extract fraction.

* * * * *